United States Patent
Tajima et al.

(10) Patent No.: US 7,029,882 B1
(45) Date of Patent: Apr. 18, 2006

(54) SUSPENSION FOR DETERMINING SEQUENCE OF GENETIC MATERIALS, METHOD OF DETERMINING THE SEQUENCE OF GENETIC MATERIALS BY USING SAME, AND METHOD FOR HIGH-SPEED SCORING SNPS

(75) Inventors: Hideji Tajima, Matsudo (JP); Mitsuo Itakura, 3-8-101, Minamiskonanabancho, Tokushima-shi, Tokushima 770-0037 (JP)

(73) Assignees: Precision System Science Co., Ltd., Matsudo (JP); Mitsuo Itakura, Tokushima (JP)

( * ) Notice: Subject to any disclaimer, the term of this patent is extended or adjusted under 35 U.S.C. 154(b) by 231 days.

(21) Appl. No.: 10/110,626

(22) PCT Filed: Oct. 11, 2000

(86) PCT No.: PCT/JP00/07050

§ 371 (c)(1),
(2), (4) Date: Aug. 19, 2002

(87) PCT Pub. No.: WO01/27320

PCT Pub. Date: Apr. 19, 2001

(30) Foreign Application Priority Data

Oct. 12, 1999 (JP) .................................. 11/290246

(51) Int. Cl.
*C12P 19/34* (2006.01)
*C07H 21/04* (2006.01)
(52) U.S. Cl. ..................................... 435/91.2; 536/24.3
(58) Field of Classification Search ................... 435/6; 536/24.3
See application file for complete search history.

(56) References Cited

U.S. PATENT DOCUMENTS

2004/0203078 A1  10/2004  Machida et al.

FOREIGN PATENT DOCUMENTS

| EP | 0721019 A2 | 7/1996 |
|---|---|---|
| JP | 8-62224 | 3/1996 |
| JP | 9-182591 | 7/1997 |
| WO | WO 95/09248 | 4/1995 |
| WO | WO 96/17957 | 6/1996 |
| WO | WO 96/41005 | 12/1996 |
| WO | WO 98/31836 | 7/1998 |
| WO | WO 99/22030 | 5/1999 |
| WO | WO 99/39003 | 8/1999 |
| WO | WO0005357 | 2/2000 |

OTHER PUBLICATIONS

Tobe et al. Single-well genotyping of diallelic sequence variations by a two-color ELISA-based oligonucleotide ligation essay. Nucl. Acids Res. vol. 24, pp. 3728-3732 (1996).*
Olsvik et al. Magnetic Separation Techniques in Diagnostic Microbiology Clinical Microbiology Reviews, vol. 7, pp. 43-54 (1994).*

* cited by examiner

Primary Examiner—John S. Brusca
(74) Attorney, Agent, or Firm—Haynes and Boone, LLP

(57) ABSTRACT

An object in relation to a suspension for determining the sequence of genetic materials, a method of determining the sequence of genetic materials using such a suspension, and a method for high-speed scoring SNPs using such a suspension, is to ensure high reliability, and substantially increase reaction efficiency, to thereby shorten the time until reaching an equilibrium.

19 Claims, 3 Drawing Sheets

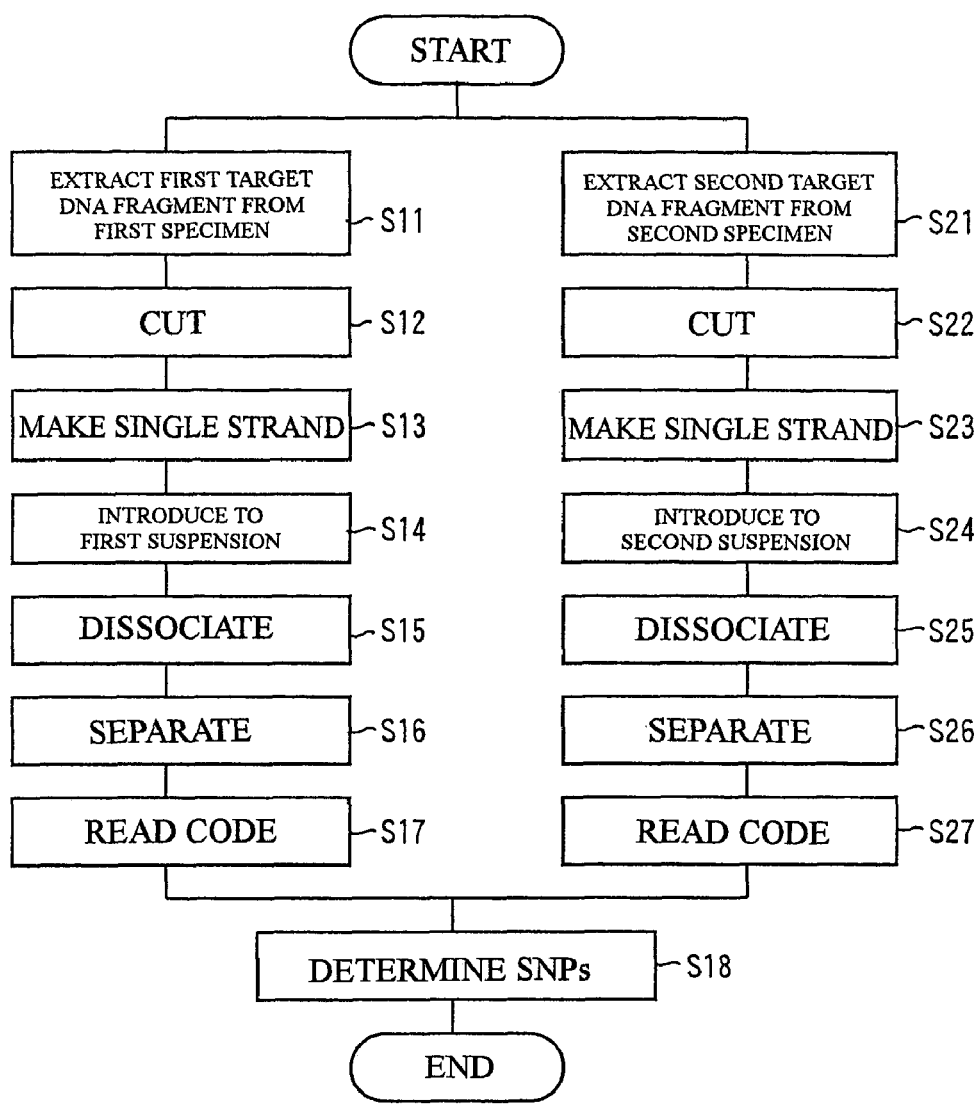

SUSPENSION FOR DETERMINING SEQUENCE OF GENETIC MATERIALS, METHOD OF DETERMINING THE SEQUENCE OF GENETIC MATERIALS BY USING SAME, AND METHOD FOR HIGH-SPEED SCORING SNPS

CROSS REFERENCED TO RELATED APPLICATIONS

This application is a national phase application of international application serial No. PCT/JP00/07050, filed Oct. 11, 2000 which claims priority to Japanese patent application Ser. No. 11/290,246, filed Oct. 12, 1999.

TECHNICAL FIELD

The present invention relates to a suspension for determining the sequence of genetic materials, a method of determining the sequence of genetic materials using such a suspension, and a method for high-speed scoring SNPs using such a suspension. More particularly, the invention relates to a suspension for determining the sequence of genetic materials, a method of determining the sequence of genetic materials using such a suspension, and a method for high-speed scoring SNPs using such a suspension, for specifying base sequences of genetic materials such as DNA fragments and the like and for specifying SNPs.

The present invention can be used; for determining or controlling base sequences of genes, in the field of agriculture, engineering, pharmacology, medicine, psychology, or the physical sciences such as chemistry biology or the like, for determining base sequences of genetic materials in various areas of medical treatment, pharmaceuticals, physiological hygiene, health, life or foodstuffs, and for clarifying relationships between base sequences of genetic materials and the form, structure, character, body type, sickness, sensitivity in relation to medicines, temperament, character and the like, of various life forms including and humans.

BACKGROUND ART

Heretofore, in order to specify SNPs (single nucleotide polymorphisms) which determine the identification and the sensitivity with respect to medicine of disease susceptible-genes of "common diseases", there is a pressing need for the development of a scoring system for highly effective SNPs detection over the whole genome. Presently, a system for detecting and scoring SNPs at high efficiency is in the development stage, and a so called DNA chip based on the principal of hybridization is only under preliminarily examination.

Incidentally, with DNA chips, a system such as that of Affymetrix, Inc. for detecting SNPs by preparing, for one of the already known SNPs which has been spotted onto a plate such as a semiconductor film or a slide glass etc., an oligonucleotide array of more than 10 types including this SNP and detecting the SNPs by whether the PCR amplified DNA fragment has been hybridized by these, has already been put to practical use.

However, the method which uses this DNA chip has a problem in that the equipment and running cost is expensive. Furthermore, for the DNA chip, since the hybridization reaction is a non-specific physicochemical reaction, a system with redundancy using this plurality of oligonucleotides is necessary. Therefore, even if this system is used, there is also a problem in that approximately 10% erroneous judgments occur.

It is an object of the present invention to resolve the abovementioned problems, with a first object being to provide a suspension for determining the sequence of genetic materials, a method of determining the sequence of genetic materials using such a suspension, and a method for high-speed scoring SNPs using such a suspension, which can increase reaction area and promote reaction in a liquid, and substantially increase reaction efficiency, to thereby shorten the time until reaching an equilibrium, by using minute particles (beads), rather than performing the conventional method of a so-called DNA chip or the like, involving a hybridization reaction on a limited narrow surface within a spot of a slide glass.

A second object is to provide a suspension for determining the sequence of genetic materials, a method of determining the sequence of genetic materials using such a suspension, and a method for high-speed scoring SNPs using such a suspension, which can reliably score base sequences without the need for duplication, by using the high specificity of enzyme reactions to differentially distinguish base sequences.

A third object is to provide a high speed highly reliable suspension for determining the sequence of genetic materials, a method of determining the sequence of genetic materials using such a suspension, and a method for high-speed scoring SNPs using such a suspension, which determines the sequence by promoting the reaction altogether under the same conditions by using various beads which have been coded, rather than by determining the sequence based on the positions of the oligonucleotides which have been immobilized on a slide glass.

DISCLOSURE OF THE INVENTION

In order to achieve the above objects, a first aspect of the invention is one where, suspended in a liquid in a container there is, a first coded oligonucleotide group which includes first coded oligonucleotides having one type of base sequence of a predetermined base number which have been coded so as to identify the base sequence thereof, so as to cover the base sequences of all the types or specific types for the base number thereof, and which are each provided so as to be sortable as one belonging to this group, a second coded oligonucleotide group which includes second coded oligonucleotides having one type of base sequence of a predetermined base number which have been coded so as to identify the base sequence thereof, so as to cover the base sequences of all the types or specific types for the base number thereof, and which are each provided so as to be sortable as one belonging to this group, and an enzyme which differentially bonds the two oligonucleotides via pair of deoxyribose being a sugar of the end nucleotide thereof, only in the case of a situation where the two coded oligonucleotides are hybridized to a single strand genetic material and the end nucleotide of the base sequence thereof are directly adjacent, and the base sequence of the predetermined base number is a constant relation with the base sequence of that genetic material.

Here the "genetic material" is mainly DNA (fragments), but this may also include RNA (fragments). "Base" means, for DNA, thymine (T), cytosine (C), adenine (A), guanine (G), while in the case of RNA, uracil (U) is introduced instead of thymine. For the "specific types", in the case where the base sequence of the target genetic material is broadly known to some extent, then rather than the base sequences of all types, the types can be reduced somewhat.

As a method of "providing so as to be sortable", there is the case of being sortable; by coding with a labeled material so as to be able to identify the two groups themselves, or making the kinds of labeled material used for the two groups different, or providing a carrier capable of remote control on the coded oligonucleotide of one group, and thus being able to move this group to an optional position by remote control. For "capable of remote control", for example there is the case of being capable of remote control: by providing a magnetic particle on the oligonucleotide and being capable of remote control by means of magnetic operation, by providing a charged particle on the oligonucleotide, or by charging the oligonucleotide itself and using an electric field.

"Coding" is performed by changing the kind(s) and/or the molar ratio(s) of the labeled material by using for example a luminescent material such as a fluorescent material, or a labeled material such as a radioactive material. Furthermore, "coded oligonucleotide" involves bonding various labeled materials to one oligonucleotide via an adaptor, or as in the seventh or eighth aspects of the invention, this involves retaining one type of several oligonucleotides and the labeled material on a carrier. Preferably, as with the seventh or eighth aspects of the invention, the labeled material is distributed and bonded to only one part of the several oligonucleotides.

Making the kind of the labeled material used in coding the first oligonucleotide and the kind of the labeled material used in coding the second oligonucleotide different is appropriate for analysis. In this case, the first oligonucleotide group and the second oligonucleotide group are sorted by coding only.

For the "enzyme" there is for example an enzyme which bonds the oligonucleotides in the case where these are directly adjacent as with DNA ligase (DNA linking enzyme). "Constant relation" means for example a complimentary relation or an identical relation.

In the first aspect of the invention, the suspension has an enzyme, which differentially bonds pair of deoxyribose, being the sugars of the end nucleotide of the oligonucleotides, only in the case of a situation where the base sequence of the predetermined base number of the two coded oligonucleotides is a constant relation to the base sequence of the genetic material. Consequently, by introducing and suspending a genetic material of a single strand of a target for which the base sequence is to be known into this enzyme system, only the oligonucleotide with a constant relation to this base sequence can be bonded. Therefore, by dissociating a single strand genetic material, and reading the code of the pair of these oligonucleotides, the target genetic material can be known with high reliability from the base sequence of the predetermined base number.

Furthermore, according to the first aspect of the invention, the two groups, namely the first coded oligonucleotide group and the second coded oligonucleotide group, each coded oligonucleotide of which has a base sequence of a predetermined base number, are used, and the enzyme which differentially bonds pair of deoxyribose being the sugar of the end nucleotide of the oligonucleotide, only in the case where there is a constant relation with the genetic material, is used. Consequently, in comparison with the case where the base sequence of the complimentary oligonucleotide is obtained by simply using the hybridization as with the DNA chip, the sequence of the genetic material can be easily determined with even greater reliability.

Moreover, the base sequence can be simply and easily determined by an operation involving suspending the oligonucleotide having the various base sequences without performing the fabrication involving fixing oligonucleotides of various modes of the base sequence to a DNA chip in order to specify SNPs.

Furthermore, with the present invention, the reaction can be performed within a wide range inside the suspension, rather than the hybridization reaction on the limited narrow flat surface within a spot on a plate such as a slide glass etc. Therefore the reaction efficiency can be substantially improved, and the time until reaching equilibrium can be shortened.

Furthermore, different to the method of distinguishing the sequence of oligonucleotides immobilized on a slide glass, by the position of the oligonucleotides, the coded various types of oligonucleotides coexist in the same reaction liquid, and hence the reactions can be proceeded altogether under the same conditions.

In the present invention, rather than determining the long base sequence all at once, short base sequence which can be distinguished are repeated and applied in order that the enzyme performs differential bonding and thereby determines the long base sequence. Consequently, the types of base sequence which are necessary for the first coded oligonucleotide group and the second coded oligonucleotide group used in the determination, is extremely small compared to the number of types of oligonucleotides necessary for determining the base sequences corresponding to the total of the base number of these. Hence the operation of coding these is easy. For example, in the beforementioned embodiment, it is sufficient if the overall base sequence type number is 64+64 giving 128. On the other hand, if the oligonucleotides for 6 base sequences are to be prepared, it is necessary to prepare $4^6=4096$ types, whereas the type number of base sequence in the invention is only very little.

A second aspect of the invention is one where, in the beforementioned aspect of the invention, the respective first coded oligonucleotides are coded so as to be sortable as those belonging to their group, and the respective second coded oligonucleotides are provided so as to be retained on magnetic particles which are remote controlled by a magnetic field, so as to be sortable as those belonging to their group.

According to the second aspect of the invention, by applying a magnetic field to inside a liquid passage of for example a nozzle of a dispenser, then these can be separated. Therefore coded oligonucleotides which do not have a magnetic particle can be removed, and hence coded oligonucleotides which have magnetic particles can be easily and reliably sorted.

A third aspect of the invention, is one where, in the respective aspects of the invention, the predetermined base number of the respective first coded oligonucleotides and second coded oligonucleotides is at least three bases, and the first coded oligonucleotide group comprises at least $4^3$ types of first coded oligonucleotides obtained by replacing the respective bases of the three bases, and the second coded oligonucleotide group comprises at least $4^3$ types of second coded oligonucleotides obtained by replacing the respective bases of the three bases.

For analysis, preferably, the respective amounts (density and absolute quantity) of the first coded oligonucleotide group and the second coded oligonucleotide group are approximately identical, and the amounts for each of the respective types in each of these groups are also approximately identical.

A fourth aspect of the invention, is one where, in the above mentioned respective aspects of the invention, the enzyme is DNA ligase, and differentially bonds the deoxyriboses being the sugar of the end nucleotide, only in the case of a situation where the end nucleotides of a base sequence comprising three or more bases of two coded oligonucleotides which have been hybridized on a single strand genetic material are directly adjacent, and the base sequences of the oligonucleotides are complementary to the base sequence of that genetic material.

Here "complementary" means a relationship such as to be able to form a base pair with each other in DNA constituting a double strand. The base pair in the DNA is adenine and thymine, and cytosine and guanine, while the base pair in RNA is adenine and uracil, and cytosine and guanine.

In the third and fourth aspects of the invention, the predetermined base number of the respective first coded oligonucleotide and second coded oligonucleotide is at least three bases. Consequently, it is sufficient if the types of the first coded oligonucleotide group and the second coded oligonucleotide group are respectively $4^3$ types, and hence it is not necessary to prepare 4096 types as with the oligonucleotides having 6 bases. Therefore, it is sufficient to prepare a substance of a very small number of types, and hence the operation is easy.

A fifth aspect of the invention is one where, in the respective aspects of the invention, the respective first coded oligonucleotides belonging to the first coded oligonucleotide group comprise an oligonucleotide of one type having a predetermined base sequence and labeled material bonded to the oligonucleotide, and the labeled material includes predetermined kinds at predetermined molar ratios respectively, and the coding is performed by changing the kind(s) and/or the molar ratio(s).

According to the fifth aspect of the invention, coding is effected by bonding the labeled material for which the kind and/or the molar ratio is changed, to the oligonucleotide. According to this aspect of the invention, oligonucleotides connected in a string corresponding to the genetic material can be obtained.

A sixth aspect of the invention is one where, in the respective aspects of the invention, for all or a part of the first coded oligonucleotide belonging to the first coded oligonucleotide group, a free end thereof has labeled dideoxyribose.

Here "free end" is the end of the ends of the oligonucleotide which is not bonded to another oligonucleotide, that is to say, the end which bonds the labeled material. The labeled dideoxyribose is bonded to the 3' end of the first coded oligonucleotide. By including dideoxyribose, then the bonding can be induced irrespective of the oligonucleotide which is adjacent thereafter.

Consequently, in the case where dideoxyribose is included in all, of the first coded oligonucleotides, and dideoxyribose is similarly included in all of the second coded oligonucleotides, and the second coded oligonucleotide has a carrier, then only a dimer for which the first coded oligonucleotide and the second oligonucleotide are connected one at a time (for each of the beforementioned predetermined base numbers) is obtained. As a result, the base sequence can be arranged, and hence for example in the case where coding is by a luminescent material, the readout of the code can be reliably and easily performed.

In the case where the dideoxyribose is included in a part of the first coded oligonucleotides, the conjugate with the first coded oligonucleotide multiply bonded once, twice, thrice or more, and finally the first coded oligonucleotide which includes the dideoxyribose bonded, can be identified. As a result, the DNA sequence can be easily read out.

According to an sixth aspect of the invention, in the case where the dideoxyribose is provided for all parts, only a dimer with the first coded oligonucleotide and the second coded oligonucleotide connected one at a time (for each of the predetermined bases) is obtained. As a result, the base sequences can be arranged, and hence for example in the case where coding is by a luminescent material, reading of the code can be reliably and easily performed. Furthermore, in the case where the dideoxyribose is provided in a part, the conjugate with the first coded oligonucleotide multiply bonded once, twice, thrice or more, and finally the first coded oligonucleotide which includes the dideoxyribose bonded, can be identified. As a result, the DNA sequence can be comparatively easily read out.

A seventh aspect of the invention is that in the respective aspects of the invention, each of the first coded oligonucleotides belonging to the first coded oligonucleotide group comprise; one non magnetic carrier, several one type of oligonucleotides having a predetermined base sequence and bonded to the carrier, and labeled materials bonded to a part of the oligonucleotides at a position different to the position to which the carrier is bonded, or bonded to the carrier at a position different to the position to which the oligonucleotide is bonded, and all of the labeled materials include predetermined kinds at predetermined molar ratios respectively, and the coding is performed by changing the kind(s) and/or the molar ratio(s) of the labeled material.

Here the bonding of the respective oligonucleotides with the carriers is performed for example by coating a bonding material which differentially bonds to the oligonucleotide, onto the carrier. For these bonding materials, for example there is a combination of biotin and avidin.

An eighth aspect of the invention is that in the respective aspects of the invention, each of the second coded oligonucleotides belonging to the second coded oligonucleotide group comprise; one magnetic carrier, several oligonucleotides of one type having a predetermined base sequence and bonded to the carrier, and labeled materials bonded to a part of the oligonucleotide at a position different to the position to which the carrier is bonded, or bonded to the carrier at a position different to the position to which the oligonucleotide is bonded, and all of the labeled materials include predetermined kinds at predetermined molar ratios respectively, and the coding is performed by changing the kind(s) and/or the molar ratio(s) of the labeled material.

The seventh and eighth aspects of the invention are that the oligonucleotide is supported on the non magnetic or magnetic carrier, and the coding is performed by changing the kind and/or the molar ratio of the labeled material bonded to a part of the oligonucleotide or the carrier. Consequently, base sequences of many types from several tens to several hundreds can be reliably and clearly coded and identified. Furthermore, the reaction area is increased by reacting on the surface of the carrier made of minute particles or the like, and hence reaction efficiency can be significantly increased.

A ninth aspect of the invention is that in the respective aspects of the invention, the oligonucleotide is bonded to the carrier or the labeled material via an arm.

The ninth aspect of the invention is that the oligonucleotide is bonded to the carrier or the labeled material via an arm. According to this aspect of the invention, there is even further separation between the labeled materials. Therefore quenching (extinction) can be effectively prevented, and hence the base sequence can be determined with high reliability.

A tenth aspect of the invention is one having: a conjugation step for introducing and suspending in the suspension according to any one of the first to the ninth aspects of the invention, a target genetic material of a single strand of a predetermined base which is sufficiently larger than the predetermined base number, for hybridizing the first coded oligonucleotide, and second coded oligonucleotide on the target genetic material; a dissociation step for again disassociating the target genetic material which has captured the first coded oligonucleotide or the second coded oligonucleotide, into a single strand; a sorting step for sorting pairs of the first coded oligonucleotide and the second coded oligonucleotide from in the suspension liquid; and a determining step for determining the base sequence of the target genetic material based on a combination of the code for identifying the base sequence showing the sorted first coded oligonucleotide, and a code for identifying the base sequence showing the second coded oligonucleotide.

Here the sorting step, in the case where the coding is performed by a luminescent material such as a fluorescent material, uses for example a flow cytometer, and only in the case where a pair of emission wavelengths of the first coded oligonucleotide and the second coded oligonucleotide exist, is the pair of oligonucleotides sorted. Furthermore, in the case where one coded oligonucleotide of the first and second group has a magnetic particle, then by applying a magnetic field to inside a liquid passage from the outside, the oligonucleotide is attached to the inner wall of the liquid passage and thus separated and sorted, and only in the case where an appropriate emission wavelength exists, is this sorted by the flow cytometer. Furthermore, by considering the emission intensity of the respective wavelengths using the flow cytometer, the number of overlap appearances can be determined.

According to the tenth aspect of the invention, an effect as already explained for the first aspect of the invention is demonstrated.

An eleventh aspect of the invention is that in the respective aspects of the invention, in the conjugation step, the first coded oligonucleotides are coded so as to be sortable as those belonging to their group, and the second coded oligonucleotides are provided so as to be retained on magnetic particles which are remote controlled by a magnetic field so as to be sortable as those belonging to their group, and the sorting step has a separation step for separating the second coded oligonucleotides by means of magnetic field operation.

According to the eleventh aspect of the invention, an effect as already explained for the second aspect of the invention is demonstrated.

A twelfth aspect of the invention is that in the respective aspects of the invention, in the case where the second coded oligonucleotides have magnetic particles as the carrier, the sorting step uses a dispenser having a liquid passage, a magnetic section for applying and removing a magnetic field to the liquid passage from the outside, and a pressure control section for controlling a pressure inside the liquid passage to draw in and discharge a liquid, and by applying or removing a magnetic field from the outside of the liquid passage, the magnetic particles which have the second coded oligonucleotides are attracted to or separated from the inner wall of the liquid passage.

According to the twelfth aspect of the invention, a dispenser having a liquid passage and a magnetic force section is used, and by applying or removing a magnetic field from the outside of the liquid passage, determination of the base sequence can be consistently performed automatically, efficiently and quickly.

A thirteenth aspect of the invention is one having: a conjugation step for preparing two approximately identical suspensions according to any one of the first to the ninth aspects of the invention, and introducing and suspending in one thereof a first target genetic material of a single strand of a predetermined base obtained by extracting from a first specimen, and introducing and suspending in the other thereof a second target genetic material of a single strand of a predetermined base obtained by extracting from a second specimen, and hybridizing the first coded oligonucleotide, and second coded oligonucleotide on respective target materials; a dissociation step for again disassociating the target genetic material which has captured each of the first coded oligonucleotide or the second coded oligonucleotide, into a single strand; a sorting step for sorting the first coded oligonucleotide and the second coded oligonucleotide from in the suspension liquid; and a determining step for determining the base sequence of the target genetic material based on each of a combination of the code for identifying the base sequence showing the sorted first coded oligonucleotide, and a code for identifying the base sequence showing the second coded oligonucleotide; and an identification step for performing identification of SNPs by comparing base sequences determined for the first target genetic material and base sequences determined for the second target genetic material. Here "approximately identical" means that at least the constituents and the amount thereof (density and absolute quantity) are approximately identical. The first coded oligonucleotide used in the seventh aspect of the invention, and the second coded oligonucleotide used in the eighth aspect of the invention are those used for the invention of Japanese Unpublished patent application (Application No. 10-206,057) and International Patent Application (PCT/JP99/03824) pending in the name of Machida Masayuki and Precision System Science (PSS) Co., Ltd.

In the thirteenth aspect of the invention, an effect as already explained for the first aspect of the invention is demonstrated.

BRIEF DESCRIPTION OF THE DRAWINGS

FIG. 3 is a flow chart showing a method of scoring SNPs according to an embodiment of the present invention.

BEST MODE FOR CARRYING OUT THE INVENTION

Figure 1:
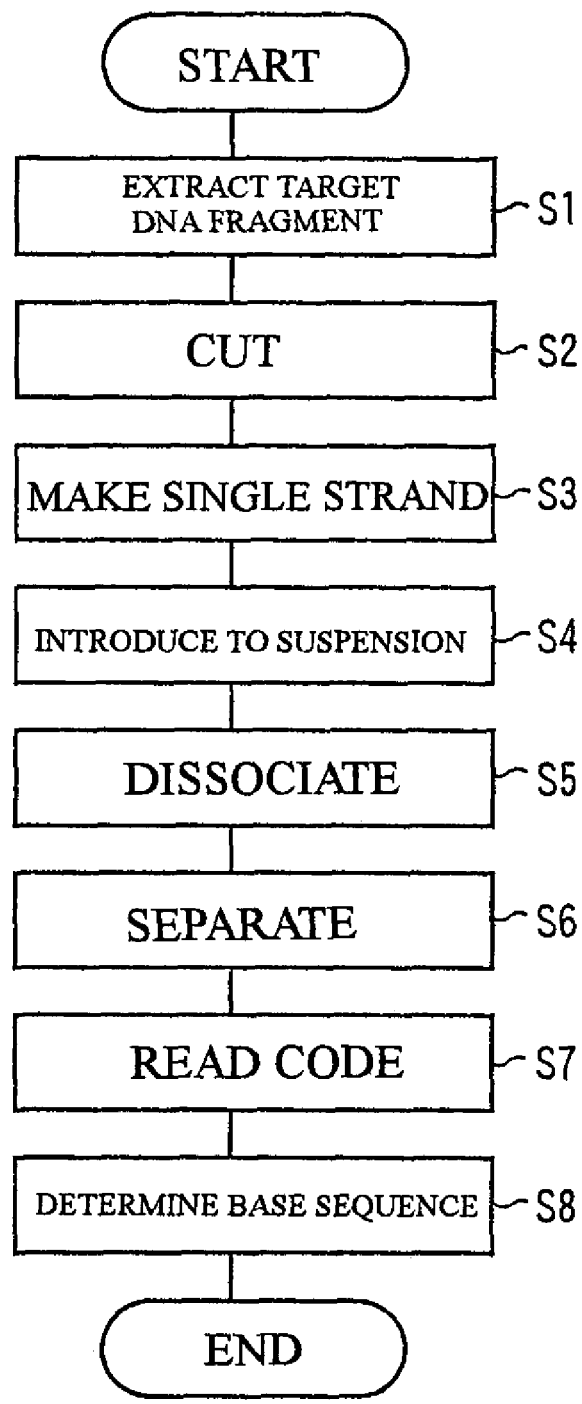
FIG. 1 is a flow chart showing a method of determining the sequence of genetic materials according to an embodiment of the present invention.

A method of determining the sequence of genetic materials method according to an embodiment of the present invention will now be described based on FIG. 1 and FIG. 2. This embodiment does not limit the present invention unless particularly specified.

The method according to this embodiment uses the following dispenser (PSS Co., Ltd. pending patent application, Japanese Patent Application No. Hei 6-157,959 and Japanese Patent Application No. Hei 7-39,425). This dispenser (not shown in the figure) is one having; a set of 8 nozzles each with a pipette tip detachably set therein, a suction/ discharge mechanism for drawing in and discharging a liquid, and a magnetic force section capable of applying and removing a magnetic field from outside of a liquid passage of the pipette tips set in the nozzle. Furthermore, this has a moving section capable of moving the dispenser and the nozzles of the dispenser along directions parallel and vertical to the plane of a stage.

Moreover, the dispenser has a control section for controlling the suction/discharge of the suction/discharge mechanism, controlling the magnetic field of the magnetic force section, and for controlling the movement. The control section has a processing device contained in a computer, an output device such as a CRT or liquid crystal etc. display section or a printer or the like, an input section such as a keyboard or mouse for setting and controlling various processing procedures and performing data input and the like, and a reader or the like for reading a recording medium such as a floppy disc, CD or MO recording medium on which is recorded a program or data, and a communication section for connecting to a communication network. Furthermore, a flow cytometer (not shown in the figure) is used for determining the DNA sequence.

Moreover, in order to determine the sequence of genetic material according to the present embodiment, a suspension as shown hereunder is held in a container.

This suspension is one where a detection oligonucleotide group as a first coded oligonucleotide group, a magnetic force controllable oligonucleotide group as a second coded oligonucleotide group, and a DNA ligase are suspended and mixed in a liquid and held in a container. Here the amounts (density and absolute quantity) of the first coded oligonucleotide and the second coded oligonucleotide are made approximately identical in order to facilitate analysis.

The detection oligonucleotide group includes detection oligonucleotides having at least one type of base sequence of base number 3 which have been coded so as to identify the base sequence thereof, so as to cover the base sequences of all of the types $4^3$ (=64) types for this base number 3, and which are each provided so as to be sortable by means of coding so as to identify this as one belonging to the group. Furthermore, the magnetic force controllable oligonucleotide group includes magnetic force controllable oligonucleotides having at least one type of base sequence of base number 3 which have been coded so as to identify the base sequence thereof, so as to cover the base sequences of all of the types $4^3$ (=64) types for this base number 3, and which are each provided so as to be sortable as one belonging to the group, by being movable by magnetic force operation. Furthermore, the amounts of each type of detection oligonucleotide and magnetic force controllable oligonucleotide are made approximately identical in order to facilitate analysis.

Moreover, the DNA ligase is an enzyme which differentially bonds deoxyribose pair, being the sugars of the end nucleotid of the base sequence, of two oligonucleotides, only in the case of a situation where the two oligonucleotides are hybridized on a single strand genetic material, and the deoxyriboses are directly adjacent, and the base sequences for each of the three bases are complementary to the base sequence of that genetic material.

The detection oligonucleotides comprises: one non magnetic carrier, several one type of this oligonucleotide having a base sequence of three bases bonded to this carrier, and a fluorescent material being a labeled material bonded to one part of the oligonucleotide at a position different to the position where the carrier is bonded, and all of the fluorescent materials retained on this carrier include predetermined kinds at predetermined molar ratios respectively, and coding for identifying $4^3$ (=64) kinds is performed by changing the kind and/or the molar ratio of the fluorescent material. Here regarding the fluorescent material, for example three kinds are used for the detection oligonucleotide, and three kinds are used for the magnetic force controllable oligonucleotide. For the kinds of the fluorescent material, there is for example FITC (fluourescein-isothiocyanate), rhodamine, isothiocyanate, IRD 40, CY 3, CY 5, europium complex and the like.

Furthermore, the magnetic force controllable oligonucleotide comprises; one magnetic carrier, several of one type of this oligonucleotide having a base sequence of three bases bonded to this carrier, and a fluorescent material being a labeled material bonded to one part of the oligonucleotide at a position different to the position where the carrier is bonded, and all of the fluorescent materials retained on this carrier include predetermined kinds at predetermined molar ratios respectively, and coding for identifying $4^3$ (=64) kinds is performed by changing the kind and/or the molar ratio of the fluorescent material. Here on the oligonucleotide used for coding, preferably IMP (inosinic acid: amino group or hydroxyl group not attached to the purine ring etc.) is provided as an arm or a spacer between the carrier or the labeled material, to thereby prevent quenching of the fluorescent material.

To continue, a method of determining the sequence of genetic materials using a suspension for determining the sequence of genetic materials, according to the present embodiment will be described based on FIG. 1.

As shown in FIG. 1, the method of determining the sequence of genetic materials involves, in step S1, extracting a target DNA fragment from a sample, for example a cell or bacteria etc. of a person, for which a base sequence of DNA is to be determined. In extracting the target DNA fragment, for example using the dispenser, a bacteria colony to which a vector has been introduced, and a DNA extraction liquid are mixed and solubilized. Then by mixing in the magnetic particles using the dispenser, target DNA fragments of a predetermined base (1 to several kilo bases) are captured on the magnetic particles. When a suspension liquid containing the magnetic particles which have captured the target DNA fragments is passed through a liquid passage of the dispenser, then by applying a magnetic field, these are attached to the inner wall of the liquid passage and separated. Then, by drawing a cleaning solution through the liquid passage, with the magnetic particles attached to the inner wall of the liquid passage, the magnetic particles and the target DNA fragments which are captured on the magnetic particles, and the liquid passage are washed. After this, the vector is eluted, with the magnetic particles still attached to the inner wall of the liquid passage.

Next, in step S2, in the vector in which the extracted ring-shaped (cyclic) target DNA fragment is incorporated, the ring-shaped target DNA fragment is cut. Here the vector contains a plasmid, a bacteriophage or the like.

The cutting step involves: drawing in a liquid via a liquid passage of the dispenser, from various holding sections in which is respectively held the vector in which the target DNA fragment is incorporated and a predetermined reagent, moving this to an holding section having a thermostatic function, and then cutting the discharged ring-shaped target DNA fragment. Furthermore, for the predetermined reagent, there is for example water, cutting buffer and nicking enzyme.

In step S3, heat is added to the liquid for suspending the target DNA fragment obtained in this way, and the liquid is then cooled quickly to thereby dissociate the target DNA fragment into a single strand.

In step S4, the liquid suspending the target DNA fragment obtained in this way, is introduced to the suspension, and the two are suspended and mixed. As a result, for each of the three bases of the base sequence of the single stranded target DNA fragment, the detection oligonucleotide which is approximately complimentary with this, or the magnetic force controllable oligonucleotide are hybridized. Thus, there is obtained via the base sequence of this target DNA fragment, only one type or two types of detection oligonucleotides, only one type or two types of magnetic force controllable oligonucleotides, or a combination of the detection oligonucleotide and the magnetic force controllable oligonucleotide. Furthermore, in this suspension liquid, target DNA fragments which are not hybridized at all, or magnetic force controllable oligonucleotides which have not been hybridized with these target DNA fragments, or detection oligonucleotides, are in a suspended condition.

In the case where a base sequence pair including three bases of the detection oligonucleotides or the magnetic force controllable oligonucleotides which are hybridized with the target DNA fragment are adjacent, then due to the behavior of the DNA ligase, in the case where each of the three bases are completely complimentary with the base sequence of the target DNA fragment, the deoxyribose pair being the sugar of the end nucleotide of this oligonucleotide is bonded, and the oligonucleotides of each of the six base sequences are obtained.

The two oligonucleotides which are hybridized to the target DNA fragments are not necessarily limited to a combination of the detection oligonucleotide and the magnetic force controllable oligonucleotide. Furthermore, the base sequence pair is not limited to being adjacent. However it is clear that there is some probability that a combination of these will always exist.

Figure 2:
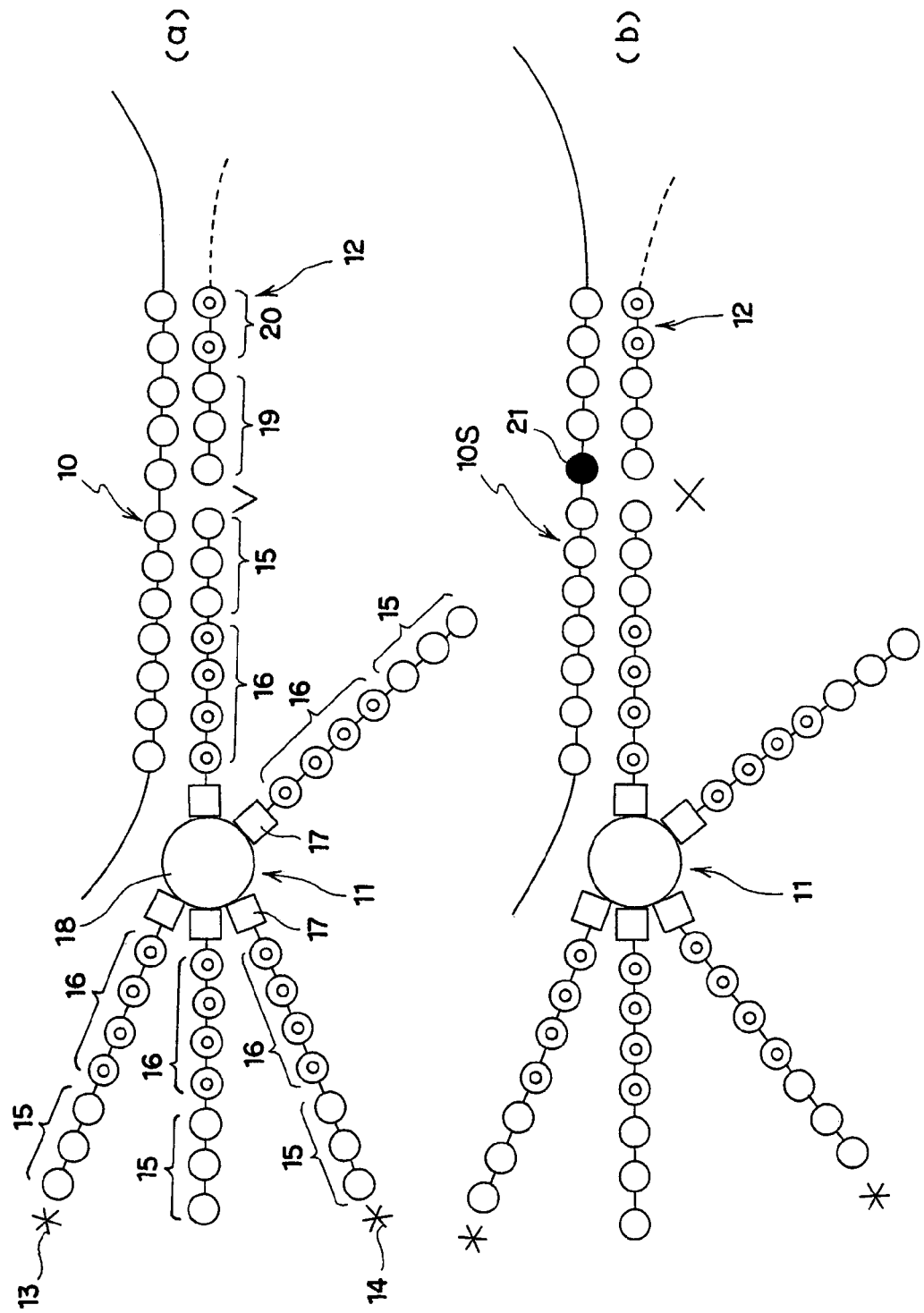
FIG. 2 is a conceptual diagram showing an oligonucleotide which has been hybridized on a target DNA fragment according to an embodiment of the present invention.

FIG. 2 shows an example of a combination of a detection oligonucleotide 12 and a magnetic force controllable oligonucleotide 11 which are hybridized on a target DNA fragment 10 which exists in a suspension liquid. FIG. 2 (a) shows a case where the base sequence for each of the three bases of the detection oligonucleotide 12 and the magnetic force controllable oligonucleotide 11 become complimentary to the base sequence of the target DNA fragment 10, and the end bases thereof are adjacent and hybridized. In this case, due to the behavior of the target DNA ligase, the deoxyribose pair being the sugar of the two end nucleotides bonds, and an oligonucleotide of six base sequences is obtained.

On the other hand, FIG. 2 (b) shows the case where the base sequence for each of the three bases of the detection oligonucleotide 12 and the magnetic force controllable oligonucleotide 11 are not complimentary with the base sequence of the target DNA fragment, and hence though end bases are adjacent and hybridized, the deoxyribose pair being the sugar of the two end nucleotides does not bond.

The small white circles in FIG. 2 show the respective bases. Furthermore, the superimposed circles show for example materials such as IMP (inosinic acid). The black circle shows a base (SNP) which is different in the target DNA fragment 10s of FIG. 2 (b), to the target DNA fragment 10 of FIG. 2 (a).

As shown in this figure, regarding the magnetic force controllable oligonucleotide 11, the multiple oligonucleotides of one type having the three bases 15 are bonded to a magnetic particle 18 being the magnetic carrier, via arms 16 and biotin 17. The surface of the magnetic particle 18 is coated with an avidin for differentially bonding with the biotin. Furthermore, fluorescent materials 13 and 14 being the labeled materials are bonded to the end nucleotides of the oligonucleotides of one part, to thereby identify these oligonucleotides. The detection oligonucleotide 12 is of a structure having three bases 19 and bonds with a non magnetic carrier, not shown in the figure, via an arm 20.

Here the "oligonucleotides of one part" are 1% or less than 10% of all of the oligonucleotides which are held by the magnetic particles 18 or non magnetic particles (not shown in the figure). Furthermore, the molar ratio is changed for example as 0.25%, 0.5%, 0.75%, and 1.0% (or 2.5%, 5.0%, 7.5% and 10.0%) so that for the respective kinds of fluorescent material, this is coded so as to identify four stages. Furthermore, by making the kinds of fluorescent material used for the detection oligonucleotide and the magnetic force controllable oligonucleotide different, then these are each sortable.

In step S5, all of the suspension liquid is drawn up by the dispenser, and transferred and discharged to an incubator which is kept in a constant temperature condition, to thus heat up the suspension. As a result, the target DNA fragments are made into a single strand, so that the oligonucleotides which are hybridized on these target DNA fragments are dissociated. At this time, in the case where, as shown in FIG. 2 (a), two oligonucleotides are bonded by the DNA ligase then oligonucleotides of six base sequences can be obtained. However as shown in FIG. 2 (b), for example even if there are two oligonucleotides which are hybridized, since these are not completely complimentary, then in the case where these are not bonded by the DNA ligase, this is suspended in the suspension as an unchanged oligonucleotide of the three base sequences. Consequently, at this stage, for the oligonucleotides having base sequences of six bases, only base sequences which have become completely complimentary to the base sequence of the target DNA fragment exist.

In step S6, when the dispenser draws up the suspension liquid, by applying a magnetic field to the interior of the liquid passage of the dispenser, then of the oligonucleotides only those which have the magnetic particles are attached to the inner wall of the liquid passage and separated. Then with the oligonucleotides attached to the inner wall of the liquid passage, by repeatedly drawing in and discharging a cleaning solution or the like, the attached oligonucleotides are washed. As a result, the single detection oligonucleotides which do not have a magnetic particle or those with the detection oligonucleotide pair bonded, or the single target DNA fragments or impurities etc. can be removed. The washed oligonucleotides still attached to the inner wall of the liquid passage of the dispenser are then transferred to another container, and by repeatedly drawing up and discharging in a condition with the magnetic field removed, the magnetic particles are removed from the inner wall of the liquid passage, and are again suspended in the liquid.

In the suspension liquid obtained in this way, there exists single magnetic force controllable oligonucleotides, the bonded single magnetic force controllable oligonucleotides, and the bonded magnetic force controllable oligonucleotides and the detection oligonucleotides.

In step S7, by passing this suspension liquid through a pipe of a flow cytometer, the code of the oligonucleotides is read out. The pipe of this flow cytometer is provided with; a light emitting device for irradiating light of a constant excitation wavelength, a light receiving device for receiving light from the excited fluorescent material, being the target material, and an analysis section for analyzing the received light.

The analysis section, in order to remove the single magnetic force controllable oligonucleotides and the bonded single magnetic force controllable oligonucleotides, sorts only the substances with the kinds of fluorescent materials, being the codes for identifying the group of detection oligonucleotides, and specifies the kinds of fluorescent material being the combinations of the codes. As a result, the combinations of the codes of the magnetic force controllable oligonucleotides and the detection oligonucleotides are read out.

In step S8, the base sequences of the six base parts which exist in the target DNA fragment can be determined from the combination of the read out codes. This code combination is determined so that the base sequence of the target DNA fragments are connected in sequence, and by determining the array, the whole of the base sequences which exist in the target DNA can be determined. In the case where the base of the target DNA fragment is longer than 4096 base sequences, or in the case where there is an array which contains a repetition, the number of overlap appearances is determined based on the emission intensity. According to this embodiment, since the light can be measured by a combination of codes of six bases each, then measurement can be performed at a high reliability.

Next is a description of a method for scoring SNPs according to the present embodiment, based on FIG. 3.

Also in this method for scoring SNPs according to the present embodiment, as mentioned before, a dispenser, a moving section, a control section, a stage and a flow cytometer are used.

In order to perform the method of scoring SNPs according to this embodiment, for simplification of analysis, the beforementioned suspensions in the same amount (density and absolute quantity) and of the same components, are prepared beforehand in two separate containers as a first suspension and a second suspension.

As shown in FIG. 3, this method for scoring SNPs is one for determining SNPs (polymorphic base sequences) by comparing base sequences of a first DNA fragment and a second DNA fragment which have been respectively extracted from two different samples, namely a first sample and a second sample.

In step S11 of FIG. 3, a vector in which a first DNA fragment of a predetermined base is incorporated is extracted from the first sample, and in step S21, a vector in which a second DNA fragment of a predetermined base is incorporated is extracted from the second sample. For the extraction method, this was previously explained for step S1. Here, regarding "predetermined base", since detection is possible in the case where several SNPs are included within the fragment, and a single SNPs exists in 300 to 500 base pairs, and a single specified six base sequence exists in an average of 4096 ($=4^6$) base pairs, then "predetermined base" is one to several kilobases.

In step S12 and step S22, each of the ring-shaped first DNA fragment and the ring-shaped second DNA fragments are cut. The method for this is as described for the beforementioned step S2.

In step S13 and step S23, heat is added to the liquid for respectively suspending the first DNA fragment and the second DNA fragment, and the liquid is then cooled quickly to make the double strand into a single strand.

In step S14 and step S24, the first DNA fragment obtained in this way is introduced to the first suspension and suspended and mixed, and the second DNA fragment is introduced to the second suspension and suspended and mixed.

In step S15 and step S25, all of the respective suspension liquids are drawn up by the dispenser, and transferred and discharged to an incubator which is kept in a constant temperature condition, to thus heat up the suspension. As a result, the first DNA fragment and the second DNA fragment are made into single strands.

In step S16 and step S26, when the dispenser draws up each of the suspension liquids, by applying a magnetic field to the interior of the liquid passage of the dispenser, then of the oligonucleotides only those which have the magnetic particles are attached to the inner wall of the liquid passage and separated. Then with the oligonucleotides attached to the inner wall of the liquid passage, by repeatedly drawing in and discharging a cleaning solution or the like, the attached oligonucleotides are washed. As a result, the single detection oligonucleotides which do not have a magnetic particle or those with the detection oligonucleotide pair bonded, or the first DNA fragments or impurities etc. can be removed. The washed oligonucleotides still attached to the inner wall of the liquid passage of the dispenser are then transferred to another container, and by repeatedly drawing up and discharging, are again suspended in the liquid.

In step S17 and step S27, in the beforementioned method using the flow cytometer, the analysis section, sorts only the substances with fluorescent materials, being the codes for identifying the group of detection oligonucleotides, in order to remove the single magnetic force controllable oligonucleotides and the bonded single magnetic force controllable oligonucleotides, and specifies the kinds of the fluorescent materials being the combinations of the codes. As a result, the combinations of the codes of the magnetic force controllable oligonucleotides and the detection oligonucleotides can be read out.

In step S18, the base sequence of the first DNA fragment and the base sequence of the second DNA fragment obtained from the combination of the read out codes are compared, and if there is one or two or more different bases, then each is an SNP(s). For example, for the first target DNA fragment 10 obtained from the first sample, there is the base sequence of FIG. 2 (a). However, if it is apparent from analysis of the code that for the second target DNA fragment 10s obtained from the second sample, the first target DNA fragment 10 and the base 21 are different, then is determined that there is polymorphism at the position of the base sequence of the base 21. According to this embodiment, the SNPs can be detected by simply observing differences in the ligase reaction product, and hence the result can be obtained easily and at high reliability.

These embodiments are specifically described in order to better understand the present invention, but are not limiting to other forms of the invention. Consequently, modification is possible within a scope wherein the gist of the invention is not changed. For example, in the above description, for the DNA fragment, propagation and extraction was performed using a vector to obtain the DNA fragment. However the invention is not limited to this case, and for example the DNA may be obtained by amplifying with a PCR method involving bonding a PCR primer to the extracted DNA fragment, or a thermally metamorphized single strand DNA may be used. Furthermore, by performing cloning, a target DNA fragment having the same base sequence may be obtained. Moreover, in performing the single stranding, instead of the method involving heating and then cooling quickly, this may be performed by adding an alkaline solution. In this case, a buffer becomes necessary.

In the above example an oligonucleotide of 128 types, that is each of $4^3$ types being all three types of predetermined base numbers is suspended. However in the case where range of these types can be narrowed down, then oligonucleotides of a specific type(s) may be suspended. Furthermore, for the predetermined base number, the description has been only for the case of three, however cases of three or more are also possible.

Moreover, for the enzyme, in the case where two oligonucleotides are hybridized adjacent to the target single strand DNA fragment, each of the three bases are distinguished, and two oligonucleotides are differentially bonded. However, the invention is not limited to this case.

Furthermore, the description has been for the case where, in determining the base sequences, six base sequences are determined from the combination of the codes by reading out the codes of the oligonucleotides one by one. However the invention is not limited to this case, and by measuring the intensity of the fluorescence or the like for a few or a large number of oligonucleotide pairs, the base sequence may be determined. Moreover, in the above examples, for the first coded oligonucleotide, one having a non magnetic carrier is used, however one not having a carrier may be used. Furthermore, for the whole or one part thereof, one provided with dideoxyribose may be used. Moreover instead of using the magnetic carrier in the second oligonucleotide, one which can be sorted by code may be used.

What is claimed is:

1. A suspension for determining the sequence of genetic materials, wherein suspended in a liquid in a container there is,
   a first coded oligonucleotide group which includes first coded oligonucleotides having one type of base sequence of a predetermined base number which have been coded by kind or molar ratio of labeled material so as to identify the base sequence thereof, so as to cover the base sequences of all the types or specific types for the base number thereof, and which are each provided so as to be sortable as one belonging to this group,
      wherein the respective first coded oligonucleotides belonging to said first coded oligonucleotide group comprise an oligonucleotide of one type having a predetermined base sequence and labeled material bonded to said oligonucleotide, and said labeled material includes predetermined kinds thereof at predetermined molar ratios respectively, and the coding is performed by changing the molar ratio of the labeled material,
   a second coded oligonucleotide group which includes second coded oligonucleotides having one type of base sequence of a predetermined base number which have been coded by kind or molar ratio of labeled material so as to identify the base sequence thereof, so as to cover the base sequences of all the types or specific types for the base number thereof, and which are each provided so as to be sortable as one belonging to this group, and
   an enzyme which differentially bonds the two coded oligonucleotides via a deoxyribose being a sugar of the end nucleotide thereof, only in the case of a situation where the two coded oligonucleotides are hybridized to a single strand genetic material and the end nucleotides of the base sequence thereof are directly adjacent, and the base sequence of said predetermined base number is a constant relation with the base sequence of that genetic material.

2. A suspension for determining the sequence of genetic materials according to claim 1, wherein said respective first coded oligonucleotides are coded so as to be sortable as those belonging to their group, and said respective second coded oligonucleotides are provided so as to be retained on magnetic particles which are remote controlled by a magnetic field, so as to be sortable as those belonging to their group.

3. A suspension for determining the sequence of genetic materials, wherein suspended in a liquid in a container there is,
   a first coded oligonucleotide group which includes first coded oligonucleotides having one type of base sequence of a predetermined base number which have been coded by molar ratio of labeled material so as to identify the base sequence thereof, so as to cover the base sequences of all the types or specific types for the base number thereof, and which are each provided so as to be sortable as one belonging to this group,
   a second coded oligonucleotide group which includes second coded oligonucleotides having one type of base sequence of a predetermined base number which have been coded by molar ratio of labeled material so as to identify the base sequence thereof, so as to cover the base sequences of all the types or specific types for the base number thereof, and which are each provided so as to be sortable as one belonging to this group,
      wherein said predetermined base number of said respective first coded oligonucleotides and second coded oligonucleotides is at least three bases, and the first coded oligonucleotide group comprises at least $4^3$ types of first coded oligonucleotides obtained by replacing the respective bases of the three bases, and the second coded oligonucleotide group comprises at least $4^3$ types of second coded oligonucleotides obtained by replacing the respective bases of the three bases, and
   an enzyme which differentially bonds the two coded oligonucleotides via a deoxyribose being a sugar of the end nucleotide thereof, only in the case of a situation where the two coded oligonucleotides are hybridized to a single strand genetic material and the end nucleotides of the base sequence thereof are directly adjacent, and the base sequence of said predetermined base number is a constant relation with the base sequence of that genetic material.

4. A suspension for determining the sequence of genetic materials according to claim 1, wherein said enzyme is DNA ligase, and differentially bonds the deoxyribose pair being the sugar of the end nucleotide, only in the case of a situation where the end nucleotide pair of a base sequence comprising three or more bases of two coded oligonucleotides which have been hybridized on a single strand genetic material are directly adjacent, and the base sequences of said oligonucleotides are complementary to the base sequence of that genetic material.

5. A method of determining the sequence of genetic materials using a suspension for determining the sequence of genetic materials, having:
   a conjugation step for introducing and suspending in the suspension, in a container there is,
   a first coded oligonucleotide group which includes first coded oligonucleotides having one type of base sequence of a predetermined base number which have been coded by molar ratio of labeled material so as to identify the base sequence thereof, so as to cover the base sequences of all the types or specific types for the base number thereof, and which are each provided so as to be sortable as one belonging to this group,
wherein the respective first coded oligonucleotides belonging to said first coded oligonucleotide group comprise an oligonucleotide of one type having a predetermined base sequence and labeled material bonded to said oligonucleotide, and said labeled material includes predetermined kinds thereof at predetermined molar ratios respectively, and the coding is performed by changing the kind and/or the molar ratio of the labeled material,
a second coded oligonucleotide group which includes second coded oligonucleotides having one type of base sequence of a predetermined base number which have been coded by molar ratio of labeled material so as to identify the bases sequence thereof, so as to cover the base sequences of all the types or specific types for the base number thereof and which are each provided so as to be sortable as one belonging to this group, and
an enzyme which differentially bonds the two coded oligonucleotides via a deoxyribose being a sugar of the end nucleotide thereof, only in the case of a situation where the two coded oligonucleotides are hybridized to a single strand genetic material and the end nucleotides of the base sequence thereof are directly adjacent, and the base sequence of said predetermined base number is a constant relation with the base sequence of that genetic material, a target genetic material of a single strand of a predetermined base number which is larger than said predetermined base number of the two coded oligonucleotides, for hybridizing said first coded oligonucleotide, and second coded oligonucleotide on said target genetic material;
a disassociation step for disassociating said target genetic material which has captured the first coded oligonucleotide or the second coded oligonucleotide, into a single stand;
a sorting step for sorting pairs of the first coded oligonucleotide and the second coded oligonucleotide from in said suspension liquid; and
a determining step for determining the base sequence of the target genetic material based on a combination of the code for identifying the base sequence showing the sorted first coded oligonucleotide, and a code for identifying the base sequence showing the second coded oligonucletide.

6. A suspension for determining the sequence of genetic materials according to claim 1, wherein for all or a part of said first coded oligonucleotides belonging to said first coded oligonucleotide group, a free end thereof has labeled dideoxyribose.

7. A suspension for determining the sequence of genetic materials according to claim 1, wherein each of the first coded oligonucleotides belonging to said first coded oligonucleotide group comprise; one non magnetic carrier, several types of oligonucleotides having a predetermined base sequence and bonded to said carrier, and labeled materials bonded to a part of said oligonucleotides at a position different from the position to which said carrier is bonded, or bonded to said carrier at a position different from the position to which the oligonucleotide is bonded, and all of said labeled materials include predetermined kinds thereof at predetermined molar ratios respectively, and the coding is performed by changing the molar ratio of the labeled material.

8. A suspension for determining the sequence of genetic materials according to claim 1, wherein each of the second coded oligonucleotides belonging to said second coded oligonucleotide group comprise; one magnetic carrier, several types of oligonucleotides having a predetermined base sequence and bonded to said carrier, and labeled materials bonded to a part of said oligonucleotides at a position different from the position to which said carrier is bonded, or bonded to said carrier at a position different from the position to which the oligonucleotide is bonded, and all of said labeled materials include predetermined kinds thereof at predetermined molar ratios respectively, and the coding is performed by changing the molar ratio of the labeled material.

9. A suspension for determining the sequence of genetic materials according to claim 7, wherein said oligonucleotide is bonded to the carrier or the labeled material via an arm.

10. A method of determining the sequence of genetic materials using a suspension for determining the sequence of genetic materials, having:
a conjugation step for introducing and suspending in the suspension, in a container there is,
a first coded oligonucleotide group which includes first coded oligonucleotides having one type of base sequence of a predetermined base number which have been coded by molar ratio of labeled material so as to identify the base sequence thereof, so as to cover the base sequences of all the types or specific types for the base number thereof, and which are each provided so as to be sortable as one belonging to this group,
a second coded oligonucleotide group which includes second coded oligonucleotides having one type of base sequence of a predetermined base number which have been coded by molar ratio of labeled material so as to identify type base sequence thereof, so as to cover the base sequences of all the types or specific types for the base number thereof, and which are each provided so as to be sortable as one belonging to this group,
wherein said predetermined base number of said respective first coded oligonucleotides and second coded oligonucleotides is at least three bases, and the first coded oligonucleotides group comprises at least $4^3$ types of first coded oligonucleotides obtained by replacing the respective bases of the three bases, and the second coded oligonucleotide group comprises at least $4^3$ types of second coded oligonucleotides obtained by replacing the respective bases of the three bases and
an enzyme which differentially bonds the two coded oligonucleotides via a deoxyribose being a sugar of the end nucleotide thereof, only in the case of a situation where the two coded oligonucleotides are hybridized to a single strand genetic material and the end nucleotides of the base sequence thereof are directly adjacent, and the base sequence of said predetermined base number is a constant relation with the base sequence of that genetic material, a target genetic material of a single strand of a predetermined base number which is larger than said predetermined base number of the two coded oligonucleotides, for hybridizing said first coded oligonucleotide, and second coded oligonucleotide on said target genetic material;
a disassociation step for disassociating said target genetic material which has captured the first coded oligonucleotide or the second coded oligonucleotide, into a single strand;
a sorting step for sorting pairs of the first coded oligonucleotide and the second coded oligonucleotide from in said suspension liquid; and a determining step for determining the base sequence of the target genetic material based on a combination of the code for identifying the base sequence showing the sorted first coded oligonucleotide, and a code for identifying the base sequence showing the second coded oligonucleotide.

11. A method of determining the sequence of genetic materials using a suspension for determining the sequence of genetic materials according to claim 10, wherein in said conjugation step, said first coded oligonucleotides are coded so as to be sortable as those belonging to their group, and said second coded oligonucleotides are provided so as to be retained on magnetic particles which are remote controlled by a magnetic field so as to be sortable as those belonging to their group, and said sorting step has a separation step for separating the second coded oligonucleotides by means of magnetic field operation.

12. A method of determining the sequence of genetic materials using a suspension for determining the sequence of genetic materials according to claim 11, wherein the case where the second coded oligonucleotides retained on magnetic particles, said sorting step uses a dispenser having a liquid passage, a magnetic section for applying and removing a magnetic field to said liquid passage from the outside, and a pressure control section for controlling a pressure inside said liquid passage to draw in and discharge a liquid, and by applying or removing a magnetic field from the outside of said liquid passage, said magnetic particles which have said second coded oligonucleotides are attracted to or separated from the inner wall of said liquid passage.

13. A method for high-speed scoring SNPs using a suspension for determining the sequence of genetic materials having:
   a conjugation step for preparing two approximately identical suspensions, in each container there is,
   a first coded oligonucleotide group which includes first coded oligonucleotides having one type of base sequence of a predetermined base number which have been coded by molar ratio of labeled material so as to identify the base sequence thereof, so as to cover the base sequences of all the types or specific types for the base number thereof, and which are each provided so as to be sortable as one belonging to this group,
   a second coded oligonucleotide group which includes second coded oligonucleotides having one type of base sequence of a predetermined base number which have been coded by molar ratio of labeled material so as to identify the base sequence thereof, so as to cover the base sequences of all the types dr specific types for the base number thereof, and which are each provided so as to be sortable as one belonging to this group,
   wherein said predetermined base number of said respective first coded oligonucleotides and second coded oligonucleotides is at least three bases, and the first coded oligonucleotide croup comprises at least $4^3$ types of first coded oligonucleotides obtained by replacing the respective bases of the three bases, and the second coded oligonucleotide group, comprises at least $4^3$ types of second coded oligonucleotides obtained by replacing the respective bases of the three bases, and
   an enzyme which differentially bonds the two coded oligonucleotides via a deoxyribose being a sugar of the end nucleotide thereof, only in the case of a situation where the two coded oligonucleotides are hybridized to a single strand genetic material and the end nucleotides of the base sequence thereof are directly adjacent, and the base sequence of said predetermined base number is a constant relation with the base sequence of that genetic material, and introducing and suspending in one thereof a first target genetic material of a single strand of a predetermined base number obtained by extracting from a first specimen, and introducing and suspending in the other thereof a second target genetic material of a single strand of a predetermined base number obtained by extracting from a second specimen, and hybridizing said first coded oligonucleotide, and second coded oligonucleotide on respective target materials;
   a disassociation step for again disassociating said target genetic material which has captured each of the first coded oligonucleotide or the second coded oligonucleotide, into a single strand;
   a sorting step for sorting the first coded oligonucleotide and the second coded oligonucleotide from in said suspension liquid; and
   a determining step for determining the base sequence of the target genetic material based on each of a combination of the code for identifying the base sequence showing the sorted first coded oligonucleotide, and a code for identifying the base sequence showing the second coded oligonucleotide; and
   an identification step for performing identification of single nucleotide polymorphisms by comparing base sequences determined for said first target genetic material and base sequences determined for said second target genetic material.

14. A method of determining the sequence of genetic materials using a suspension for determining the sequence of genetic materials according to claim 10, wherein the case where the second coded oligonucleotides are retained on magnetic particles, said sorting step uses a dispenser having a liquid passage, a magnetic section for applying and removing a magnetic field to said liquid passage from the outside, and a pressure control section for controlling a pressure inside said liquid passage to draw in and discharge liquid, and by applying or removing a magnetic field from the outside of said liquid passage, said magnetic particles which have said second coded oligonucleotides are attracted to or separated from the inner wall of said liquid passage.

15. A suspension for determining the sequence of genetic materials according to claim 3, wherein said enzyme is DNA ligase, and differentially bonds the deoxyribose pair being the sugar of the end nucleotide, only in the case of a situation where the end nucleotide pair of a base sequence comprising three or more bases of two coded oligonucleotides which have been hybridized on a single strand genetic material are directly adjacent, and the base sequences of said oligonucleotides are complementary to the base sequence of that genetic material.

16. A suspension for determining the sequence of genetic materials according to claim 3, wherein for all or a part of said first coded oligonucleotides belonging to said first coded oligonucleotide group, a free end thereof has labeled dideoxyribose.

17. A suspension for determining the sequence of genetic materials according to claim 3, wherein each of the first coded oligonucleotides belonging to said first coded oligonucleotide group comprise; one non magnetic carrier, several types of oligonucleotides having a predetermined base sequence and bonded to said carrier, and labeled materials bonded to a part of said oligonucleotides at a position different from the position to which said carrier is bonded, or bonded to said carrier at a position different from the position to which the oligonucleotide is bonded, and all of said labeled materials include predetermined kinds thereof at predetermined molar ratios respectively, and the coding is performed by changing the molar ratio of the labeled material.

18. A suspension for determining the sequence of genetic materials according to claim 3, wherein each of the second coded oligonucleotides belonging to said second coded oligonucleotide group comprise; one magnetic carrier, several types of oligonucleotides having a predetermined base sequence and bonded to said carrier, and labeled materials bonded to a part of said oligonucleotides at a position different from the position to which said carrier is bonded, or bonded to said carrier at a position different from the position to which the oligonucleotide is bonded, and all of said labeled materials include predetermined kinds thereof at predetermined molar ratios respectively, and the coding is performed by changing the molar ratio of the labeled material.

19. A method of determining the sequence of genetic materials using a suspension for determining the sequence of genetic materials according to claim 5, wherein in said conjugation step, said first coded oligonucleotides are coded so as to be sortable as those belonging to their group, and said second coded oligonucleotides are provided so as to be retained on magnetic particles which are remote controlled by a magnetic field so as to be sortable as those belonging to their group, and said sorting step has a separation step for separating the second coded oligonucleotides by means of magnetic field operation.

* * * * *